(12) United States Patent
Merger et al.

(10) Patent No.: US 6,362,332 B1
(45) Date of Patent: Mar. 26, 2002

(54) COPRODUCTION OF A CYCLIC LACTAM AND A CYCLIC AMINE

(75) Inventors: Martin Merger, Frankenthal; Rolf Fischer, Heidelberg; Andreas Ansmann, Wiesloch, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/786,914

(22) PCT Filed: Sep. 10, 1999

(86) PCT No.: PCT/EP99/06690

§ 371 Date: Mar. 12, 2001

§ 102(e) Date: Mar. 12, 2001

(87) PCT Pub. No.: WO00/17168

PCT Pub. Date: Mar. 30, 2000

(30) Foreign Application Priority Data

Sep. 18, 1998 (DE) .......................................... 198 42 900

(51) Int. Cl.⁷ .................... C07D 223/10; C07D 295/02; C07D 207/12; C07D 211/02; C07D 201/02
(52) U.S. Cl. ........................ 540/538; 540/450; 540/451; 540/612; 546/184; 546/243; 548/543; 548/579
(58) Field of Search .................................. 540/538, 612, 540/451, 450; 546/243, 184; 548/543, 579

(56) References Cited

U.S. PATENT DOCUMENTS

| | | | |
|---|---|---|---|
| 3,634,346 A | 1/1972 | McKeon | 260/239.3 |
| 3,830,800 A | 8/1974 | Brake | 260/239 B |
| 3,903,079 A | 9/1975 | Heinz | 260/239 B |
| B 470,900 | 3/1976 | Hershman | 260/239 B |
| 4,229,346 A | 10/1980 | Toussaint | 260/239 B |
| 4,290,946 A | 9/1981 | Takahashi | 260/239 B |

FOREIGN PATENT DOCUMENTS

| | | |
|---|---|---|
| CA | 920 606 | 8/1973 |
| EP | 371 492 | 6/1990 |
| EP | 372 492 | 6/1990 |
| GB | 1 358 862 | 7/1974 |

OTHER PUBLICATIONS

Chem.Ber.109, 3707–3727 (1976) Heyns et al.
Syn.Com., 18(12), 1331–1337 (1988) Wenkert et al.
Tetrahedron Lett. 29, 1988, 6913–16, Moriarty et al.

*Primary Examiner*—Bruck Kifle
(74) *Attorney, Agent, or Firm*—Keil & Weinkauf

(57) ABSTRACT

A cyclic lactam and a cyclic amine are coproduced by reacting an aliphatic alpha, omega-diamine with water in the gas phase in the presence of a heterogeneous catalyst.

5 Claims, No Drawings

COPRODUCTION OF A CYCLIC LACTAM AND A CYCLIC AMINE

The present invention relates to a process for coproducing a cyclic lactam and a cyclic amine by reacting an aliphatic alpha, omega-diamine with water in the gas phase in the presence of a heterogeneous catalyst.

Cyclic lactams, such as caprolactam, are known starting materials for the manufacture of industrially important plastics such as nylon. Cyclic amines, such as azepan, are widely used as intermediates for preparing pharmaceuticals, agrochemicals, corrosion inhibitors for nonferrous metals, vulcanization accelerants and as ingredients of textile assistants and sizes, antistats and finishes and also crosslinking agents for resins.

GB 1 358 862 (1974) discloses the preparation of lactams from specifically five- and more highly membered azacycloalkanes or from diamines and water over solid hydrogenation catalysts in the liquid phase at 150–400° C.

It is reported that piperidine/$H_2O$/$NH_3$ in a weight ratio of 1/10/9 (molar ratio about 1/47/45) converts at 300° C. over Ra-Ni, Pt/C and Ru/$Al_2O_3$ into piperidone with yields of around 50% in the course of 2–3 hours. In contrast, azepan ("hexamethyleneimine", HMI)/$H_2O$/$NH_3$ likewise in a weight ratio of 1/10/9 converts at 270° C. over Ra-Ni into only 17.6% of the theoretical amount of caprolactam in the course of 5 hours.

When the diamine used is hexamethylenediamine ("HMD"), the yield of caprolactam is at 10.7% even lower than from azepan and hence far below the industrially required level; azepan is evidently not formed in this reaction. In addition, large amounts of $NH_3$ have to be used.

Processes for preparing azacycloalkanes from diamines, such as azepan from HMD, without the coproduction of cyclic lactams are common knowledge.

For instance, CA-A 920 606 describes the conversion of HMD into azepan over cobalt and nickel catalysts (Ra type and also on supports such as $SiO_2$, $Al_2O_3$) in the presence of $H_2$ at HMD/$H_2$=1:2–70, 150–250° C. and 1–20 bar.

Azepan selectivities of up to about 90% are obtained with incomplete conversions (up to 44%). By-products formed are predominantly bishexamethylenetriamine and polyamines.

According to U.S. Pat. No. 3,830,800, HMD in a solvent such as dioxane over $RuO_2$/C likewise gives a good azepan selectivity of 91% only at low conversions (<50%).

DE-A 24 14 930 describes the HMD condensation over metals selected from the group consisting of Ni, Co, Fe, Mn, Ag, Cu, Pd as active components, with or without supports such as $Al_2O_3$ or $SiO_2$, in a high boiling solvent at 200° C. with simultaneous continuous distillative removal of the resulting azepan (boiling point 139° C. at atmospheric pressure) from the reaction mixture. Yields of up to 94% are reported.

DE-A 25 32 871 relates to the continuous condensation of HMD in an inert solvent over Ni or Co, with or without supports such as $Al_2O_3$ or $SiO_2$, at 80–150° C., the formation of oligo- and polyamines being prevented by continuously removing the azepan from the reaction mixture by azeotropic distillation with $H_2O$.

U.S. Pat. No. 3,903,079 discloses condensing HMD by using HMD/$NH_3$=1:15–30 (1:>2) at 250–400° C. over zeolites, loaded with 0.3–7% of metal cations selected from the group consisting of Cu, Pd, Mn, Ni or Cr, in the gas phase in a fixed bed or fluidized bed reactor to obtain azepan in yields of around 75%.

U.S. Pat. No. 470,900 describes the gas phase condensation of diamines to azacycloalkanes, including HMD to azepan, at 100–250° C. over Ni, Co, Fe or copper catalysts on supports without the use of $NH_3$.

An HMD/$H_2$ ratio of 1:20, 150° C. and a space velocity of 0.2 gave azepan yields of 90% over Ni/kieselguhr, while an azepan yield of 95% was obtained at an HMD/$H_2$ ratio of 1:20, 150° C. and a space velocity of 0.1 over Cu/kieselguhr.

EP-A 372 492 discloses preparing azepan from HMD at 160–260° C. in the presence of water vapor and hydrogen over Pd/$Al_2O_3$ in the gas phase at a weight ratio of HMD to water of 20:80 to 99:1. Azepan yields of 92% were obtained.

Processes for converting cyclic amines, such as azepan, into cyclic lactams, such as caprolactam, are likewise known.

According to Chem. Ber. 109 (1976) 3707–27, pyrrolidine can be reacted with oxygen under Pt catalysis to obtain pyrrolidone in yields of 60%; for other cyclic amines, however, the same reaction leads to an utterly confusing product mixture.

U.S. Pat. No. 3,634,346 describes the conversion of a cyclic amine into the corresponding cyclic lactam by oxidation with a hydroperoxide in the presence of a metal ion catalyst. The best yields obtainable with this process (15.5% of 2-pyrrolidone from pyrrolidine), however, are completely unsatisfactory for industrial processes.

Processes for oxidizing cyclic amines to the corresponding cyclic lactams using Hg(II) compounds as described in U.S. Pat. No. 3,336,299 and Synth. Commun. 18 (1988) 1331–37 are completely unsatisfactory with regard to the yield and problematical with regard to the workup and disposal of the mercurial reaction residues.

This also applies to the oxidation with iodosobenzene described in Tetrahedron Lett. 29 (1988) 6913–16.

Moreover, in the train of new developments relating to the coproduction of caprolactam and HMD on the basis of butadiene via adiponitrile ("ADN") and aminocapronitrile ("ACN"), there are economic incentives for transforming HMD into caprolactam. The partial hydrogenation of HDM to ACN and HMD can give rise, at the product separation stage, to fractions whose on-spec purification to remove by-products, for example tetrahydroazepine, presents difficulties. A simple process for converting such product fractions into readily removable, economically useful products can contribute to the flexibility of the overall process.

It is an object of the present invention to provide a process for converting an aliphatic alpha, omega-diamine into a cyclic amine and a cyclic lactam in a technically simple and economical manner.

We have found that this object is achieved by the process defined at the beginning.

The starting materials used in the process of the invention are preferably aliphatic alpha, omega-diamines of the general formula (I)

$$H_2N-(CH_2)_n-NH_2 \qquad (1)$$

where n is 4, 5, 6 or 7, i.e., 1,4-diaminobutane, 1,5-diaminopentane, 1,6-diaminohexane ("hexamethylenediamine", "HMD") and 1,7-diaminoheptane, most preferably 1,6-diaminohexane, or mixtures of such diamines (I).

The diamines may bear one or more substituents on the carbon, such as $C_1$–$C_6$-alkyl groups, cycloalkyl groups, such as cyclopentyl, cyclohexyl or cycloheptyl groups, or halogen. Preferably, the diamines are unsubstituted.

Such diamines and processes for their preparation are common knowledge.

According to the invention, the reaction is carried out in the presence of a heterogeneous catalyst or of mixtures of such catalysts.

The heterogeneous catalysts used are preferably those comprising (a) a dehydrogenating component (II) and
(b) an acidic and/or amphoteric component (III).

A suitable dehydrogenating component (II) is a metal selected from the group consisting of Cu, Ag, Ni, Co, Rh, Ru, Ir, Os and Re, preferably from the group consisting of Cu, Ag, Ni, Co, Rh and Ru, especially from the group consisting of Cu, Co and Ru, or mixtures thereof.

Component (III) can be advantageously selected from oxides, oxide hydrates, silicates, phosphates, heteropolyacids or acidic zeolites of the metals Mg, Al, B, Ti, Zr, Hf, V, Nb, Ta, Mo, W, Fe, Cr, Ge, Zn, Sn, Bi, Th, U or of the lanthanides such as La and Ce, preferably $SiO_2$, gamma-$Al_2O_3$, Nb-, Ta-, Zr-oxides and also phosphates of La, Nb, Zr, Al and B, or mixtures thereof, in which case the acidity of these compounds can be enhanced by doping with organic or preferably inorganic acids such as phosphoric acid, sulfuric acid or halohydric acids, if desired.

The dehydrogenating component (II) can be used in the form of an unsupported catalyst, for example as Raney nickel or Raney cobalt, or preferably as a supported catalyst. A useful support material is an inert material, such as C, steatite or alpha-$Al_2O_3$, preferably an acidic and/or amphoteric component, such as a component (III), especially $SiO_2$, gamma-$Al_2O_3$, Nb-, Ta-, Zr-oxides and also phosphates of La, Nb, Zr, Al and B, or mixtures thereof.

The mixing ratios of the dehydrogenating component (II) to the component (III) are readily and easily determinable by a skilled person according to the desired reaction parameters, such as product ratio or catalyst activity, by means of a few simple preliminary experiments. Suitable weight ratios of component (II) to component (III) are generally within the range from 0.1:99.9 to 50:50, preferably within the range from 0.5:99.5 to 15:85.

Water is used in the process of the invention, advantageously in a molar ratio to the diamine (I) of greater than 1, preferably in a molar ratio of water to diamine (I) of from 3:1 to 25:1, especially from 5:1 to 20:1.

The reaction mixture may advantageously have added to it an inert gas, such as nitrogen, argon, CO or methane, preferably in a molar ratio of inert gas to diamine (I) of from 5:1 to 100:1, in which case it is advantageous that the higher the molar ratio of water to diamine (I), the lower the molar ratio of inert gas to diamine (I) which can be used.

It is similarly advantageously possible for the inert gas which may be added to the reaction mixture to be hydrogen, which from experience to date has the effect of prolonging the onstream time of the heterogeneous catalyst, the molar ratio of hydrogen to diamine (I) being preferably within the range from 0.01:1 to 10:1, especially within the range from 0.01:1 to 5:1. In this connection it is to be noted that, by raising the molar ratio of hydrogen to diamine (I) especially in the case of very hydrogenation active components (II), especially Ni, Pt or Pd, it is possible to shift the product ratio of cyclic amine to cyclic lactam in favor of the cyclic amine.

The process of the invention can be carried out at from 150 to 600° C., advantageously at from 150 to 400° C., preferably at from 175 to 350° C., especially at from 180 to 300° C., and pressures from 0.1 to 2 bar, preferably from 0.75 to 1.5 bar, especially 0.9 to 1.1 bar, in a customary reactor suitable for the purpose, such as a fixed bed reactor or a fluidized bed reactor.

The workup of the product mixture can be effected in a conventional manner, for example extractively and/or preferably distillatively.

The process of the invention provides a cyclic lactam, preferably a cyclic lactam of the formula (IV)

(IV)

or a mixture of such lactams, together with a cyclic amine, preferably a cyclic amine of the formula (V)

(V)

or a mixture of such amines, n in the formulae (IV) and (V) being an integer having a value of 4, 5, 6 or 7; that is, this means in the case of the lactams (IV) azolan-2-one ("2-pyrrolidone", "gamma-butyrolactam"), azixan-2-one ("piperidin-2-one", "valerolactam"), azepan-2-one ("caprolactam"), azacyclooctan-2-one, most preferably caprolactam, or mixtures of such lactams (IV) and in the case of the amines (V) azolan ("pyrrolidine"), azixan ("piperidine"), azepan ("hexamethyleneimine", "HMI"), azacyclooctane, most preferably azepan, or mixtures of such amines (V).

The amine (V) obtained in the process of the invention, as well as being useful for the industrial applications already mentioned, may with advantage be converted into the corresponding lactam (IV), preferably by recycling into the process of the invention, especially in a mixture with the corresponding aliphatic alpha, omega-diamine (I).

The conversion may with advantage be carried out in the presence of the heterogeneous catalyst mentioned under the reaction and process conditions mentioned for the process of the invention.

EXAMPLES

Example 1

An aqueous solution of HMD (25% by weight) was evaporated and passed downwardly at 300° C. through 100 ml of Ru/$TiO_2$ (3 mm extrudates, from 0.5 to 1.5 cm in length, internal diameter of reactor 29 mm) together with 10 l/h of $H_2$ (100 l/l of catalyst·h) and 40 l/h of $N_2$ (400 l/l of catalyst·h) at a loading of 100 g/l of catalyst·h (corresponding to 25 g of HMD per liter per hour).

The effluent condensed in cold traps was analyzed by GC and was found to contain caprolactam corresponding to a selectivity of 50.2% and azepan corresponding to a selectivity of 33.7%, from a conversion rate of 88.1%.

Example 2

An aqueous solution of HMD (50% by weight) was evaporated and passed downwardly at 275° C. through 100 ml of Cu/$Al_2O_3$ (3 mm extrudates, from 0.5 to 1.5 cm in length, internal diameter of reactor 29 mm) together with 10 l/h of $H_2$ (100 l/l of catalyst·h) at a loading of 100 g/l of catalyst·h (corresponding to 50 g of HMD per liter per hour).

The effluent condensed in cold traps was analyzed by GC and was found to contain caprolactam corresponding to a selectivity of 32.2% and azepan corresponding to a selectivity of 56.3%, from complete conversion.

Example 3

An aqueous solution of HMD (10% by weight) was evaporated and passed downwardly at 300° C. through 100 ml of Ru/TiO$_2$ (3 mm extrudates, from 0.5 to 1.5 cm in length, internal diameter of reactor 29 mm) together with 80 l/h of H$_2$ (800 l/l of catalyst·h) at a loading of 100 g/l of catalyst (corresponding to 10 g of HMD per liter per hour).

The effluent condensed in cold traps was analyzed by GC and was found to contain caprolactam corresponding to a selectivity of 67.1% and azepan corresponding to a selectivity of 22.8%, from a conversion rate of 59.6%.

We claim:

1. The process for coproducing a cyclic lactam and a cyclic amine by reacting an aliphatic alpha, omega-diamine selected from the group consisting of 1,4-diaminobutane, 1,5-diaminopentane, 1,6-diaminohexane, 1,7-diaminoheptane and mixtures thereof with water in the gas phase in the presence of a heterogeneous catalyst by using a molar ratio of water to the aliphatic alpha, omega-diamine greater than 1, a temperature within the range from 150 to 600° C. and a heterogeneous catalyst comprising (a) a dehydrogenating component and
  (b) an acidic and/or amphoteric component, the dehydrogenating component in the heterogeneous catalyst being a metal selected from the group consisting of Cu, Ag, Ni, Co, Rh, Ru, Ir, Os and Re.

2. The process of claim 1, wherein hexamethylenediamine is used as aliphatic alpha, omega-diamine to obtain caprolactam as cyclic lactam and azepan as cyclic amine.

3. The process of claim 1, wherein the molar ratio of water to the aliphatic alpha, omega-diamine is within the range from 3 to 25.

4. The process of claim 1, wherein the dehydrogenating component in the heterogeneous catalyst is a metal selected from the group consisting of Cu, Co and Ru.

5. The process of claim 1, wherein the cyclic amine obtained as product is mixed into the aliphatic alpha, omega-diamine.

* * * * *